United States Patent [19]

Hayashi et al.

[11] Patent Number: 4,457,916

[45] Date of Patent: Jul. 3, 1984

[54] METHOD FOR STABILIZING TUMOR NECROSIS FACTOR AND A STABLE AQUEOUS SOLUTION OR POWDER CONTAINING THE SAME

[75] Inventors: Hiroshi Hayashi, Fuji, Masanobu Komiya, Nagaokakyo, both of Japan

[73] Assignees: Asahi Kasei Kogyo Kabushiki Kaisha, Dainippon Pharmaceutical, both of Osaka, Japan

[21] Appl. No.: 524,540

[22] Filed: Aug. 19, 1983

[30] Foreign Application Priority Data

Aug. 31, 1982 [JP] Japan ............................... 57-149890
Sep. 28, 1982 [JP] Japan ............................... 57-172178

[51] Int. Cl.$^3$ ...................... A61K 35/16; A61K 35/12
[52] U.S. Cl. ......................................... 424/101; 424/95
[58] Field of Search ................................. 424/95, 101

[56] References Cited

U.S. PATENT DOCUMENTS 4,309,418  1/1982  Green .................................. 424/101

OTHER PUBLICATIONS

Ruff et al., J. Immunol., vol. 125, No. 4 (1980), pp. 1671-1677.

Gifford et al., Chem. Abst., vol. 93 (1980), p. 147,902Z.

*Primary Examiner*—Sam Rosen
*Attorney, Agent, or Firm*—Pennie & Edmonds

[57] ABSTRACT

A method for stabilizing Tumor Necrosis Factor (TNF), which comprises adding a stabilizing agent selected from a nonionic surfactant, at least one substance selected from the group consisting of D-glucose, D-galactose, D-xylose, D-glucuronic acid, a salt of D-glucuronic acid, trehalose, a dextran and a hydroxyethyl starch, and mixtures thereof to an aqueous solution or powder containing TNF, and a stable aqueous solution or powder which contains TNF and an effective amount of such a stabilizing agent selected from a nonionic surfactant, a specific sugar or sugar-related compound and mixtures thereof. The aqueous solution or powder containing TNF can be stored for a prolonged period of time without losing its activity, and is stable on freezing, thawing, lyophilization, heat-treatment or the like.

76 Claims, 6 Drawing Figures

Concentration of Polyoxyethylene (23) lauryl ether (Brij 35)

Concentration of Polyoxyethylene (60) hydrogenated castor oil (NIKKOL HCO-60)

Concentration of Polyoxyethylene polyoxypropylene block polymer (Pluronic F 68)

Concentration of Trehalose

METHOD FOR STABILIZING TUMOR NECROSIS FACTOR AND A STABLE AQUEOUS SOLUTION OR POWDER CONTAINING THE SAME

This invention relates to a method for stabilizing Tumor Necrosis Factor, and more particularly to a method for stabilizing Tumor Necrosis Factor, in which a stabilizing agent selected from a nonionic surfactant, a specific sugar, a sugar-related compound, and mixtures thereof is added to an aqueous solution or powder containing Tumor Necrosis Factor. This invention also relates to a stable aqueous solution or powder which contains Tumor Necrosis Factor and an effective amount of the stabilizing agent selected from a nonionic surfactant, a specific sugar, a sugar-related compound, and mixtures thereof.

Carswell et al. discovered a Tumor Necrosis Factor (hereinafter simply referred to as "TNF"). They reported that TNF is a substance found in the serum of endotoxin-treated mice, rats or rabbits which had been sensitized with an immunopotentiator such as bacillus Calmette-Guerin (BCG), Corynebacteria or Zymosan, and that TNF induces necrosis in a variety of transplanted mouse tumors, with no toxic effect upon the tumor-bearing recipient [see Proc. Nat. Acad. Sci. USA, 72(9), 3666–3670(1975)].

Thereafter, numerous reports have been published with respect to the biochemical and physiological properties of mouse TNF and rabbit TNF [see, for example, Proc. Nat. Acad. Sci. USA, 73(2), 381–385(1976); Expl. Cell Biol., 47, 53–60 (1979); Br. J. Cancer, 38, 302–309(1978); and ibid., 42, 416–422(1980)]. It is noted that a cytotoxic factor, which is a substance suggested to be identical with TNF, has also been reported by some researchers [see, for example, Infect. Immun., 28(1), 204–211(1980)].

The production in vitro of TNF has also been reported. For example, Matthews determined and reported the optimal conditions under which TNF is produced in vitro by the mononuclear phagocytes from various tissues of normal and BCG-injected rabbits [see, Br. J. Cancer, 44, 418–424(1981)]. According to his report, the optimal amounts of TNF are produced by mononuclear phagocytes in the presence of endotoxin, and alveolar and peritoneal macrophages are the most potent producers of TNF. Further, according to his report, the macrophages from BCG-injected rabbits produce significantly more TNF than those from normal animals. Meanwhile, Männel et al. reported that the macrophage-enriched peritoneal exudate cells from BCG-infected mice release a cytotoxic factor when stimulated in vitro with lipopolysaccharide (endotoxin) [see, Infect. Immun., 30(2), 523–530(1980); and ibid., 33(1), 156–164(1981)].

With respect to the characteristic properties of TNF, it is known that TNF, in addition to its activity of inducing necrosis in a variety of tumors, exerts an activity not specific to the species of creatures. For example, rabbit TNF can induce necrosis in mouse tumors. Further, it is known that TNF, in vitro, does not impose any significant cytotoxic effect on the normal cells and has a cytotoxic effect on certain kinds of neoplastic cell lines (for example, L-M and Meth-A cells). As stated above, TNF has an antitumor activity, exerts an activity not specific to the species of creatures and does not impose any significant harmful effect on the normal cells. Therefore, expectations for the clinical application of TNF as an antitumor medicine have been great in the art.

It is also known that only a very small amount of TNF is induced in a mammal or tissue culture system. Accordingly, in order to ensure the wide and safe clinical application of TNF as an antitumor medicine, it is absolutely necessary to isolate and highly purify the crude TNF induced in a mammal or tissue culture system. Further, when large-scale production of the TNF to be used as an antitumor medicine is performed, it is usually needed to store the highly purified TNF in the form of a solution or a frozen mass over a prolonged period of time and lyophilize the TNF solution. However, the present inventors have found that the activity of highly purified TNF markedly drops on storing, freezing, thawing and lyophilizing it.

As far as the present inventors are aware, there has been no report in which the stability of highly purified TNF is studied. Under these circumstances, the efficient and steady supply of highly purified TNF, especially on a commercial scale cannot be ensured, despite the knowledge that TNF is an effective antitumor medicine.

To overcome the above-elucidated difficulty with respect to the stability of TNF, the present inventors have made extensive and intensive studies. As a result, it has been found, quite surprisingly, that addition of an effective amount of a nonionic surfactant, a specific sugar, a sugar-related compound, and mixtures thereof as a stabilizing agent to an aqueous solution or powder containing TNF enables the TNF to be stored over a prolonged period of time without losing its activity and renders the TNF stable on freezing, thawing, lyophilization, heat-treatment or the like. Based on this novel finding, the present inventors have completed this invention.

It is, therefore, an object of the present invention to provide a method for stabilizing TNF.

It is another object of the present invention to provide a stable TNF solution or powder which maintains its activity over a prolonged period of time and which is stable on freezing, thawing, lyophilization, heat-treatment or the like.

The foregoing and other objects, features and advantages of the present invention will be apparent to those skilled in the art from the following detailed description and appended claims taken in connection with the accompanying drawings in which:

Figure 1:
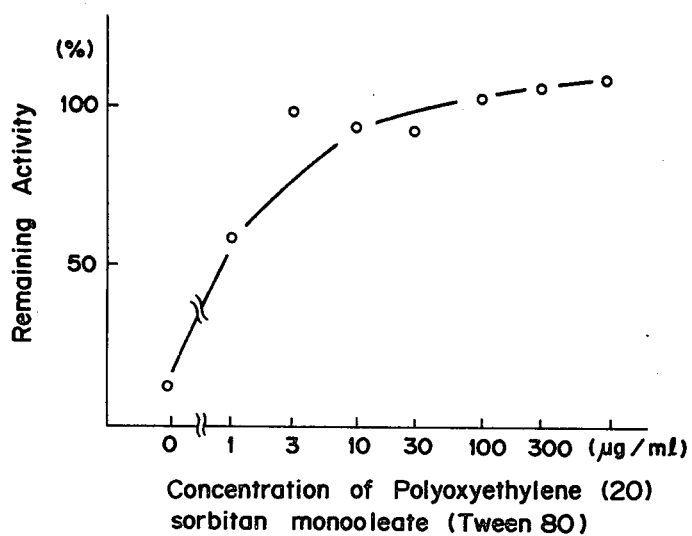
FIG. 1 is a graph showing the effect of the concentration of polyoxyethylene (20) sorbitan monooleate (Tween 80) on the remaining activity of TNF after storage at 4° C. for 7 days.

A further detailed explanation of the Figures will be given later with respect to Example 3.

In one aspect of the present invention, there is provided a method for stabilizing TNF, which comprises adding to an aqueous solution or powder containing TNF an effective amount of a stabilizing agent selected from a nonionic surfactant, at least one substance selected from the group consisting of D-glucose, D-galactose, D-xylose, D-glucuronic acid, a salt of D-glucuronic acid, trehalose, a dextran and a hydroxyethyl starch, and mixtures thereof.

In another aspect of the present invention, there is provided a stable aqueous solution or powder which contains TNF and an effective amount of a stabilizing agent selected from a nonionic surfactant, at least one substance selected from the group consisting of D-glucose, D-galactose, D-xylose, D-glucuronic acid, a salt of D-glucuronic acid, trehalose, a dextran and a hydroxyethyl starch, and mixtures thereof.

The term "TNF" as used herein denotes a physiologically active substance that is induced by administering at least one substance having a capacity for stimulating the reticuloendothelial system to a mammal and then injecting endotoxin from a Gram-negative bacterium into the mammal, or by adding endotoxin from a Gram-negative bacterium to a tissue culture system containing activated macrophages from a mammal, which substance causes necrosis of some tumors when passively transferred to tumor-bearing mammals, or a substance produced by any method and having the properties similar to those of the above physiologically active substance.

TNF to be employed in the present invention is produced by a plurality of processes known in the art, including the process of Matthews et al. [see Br. J. Cancer, 42, 416–422 (1980)] and the process of Green et al. [see J. Natl. Cancer Inst., 59(5), 1519–1522(1977)].

Typical procedures for preparing TNF to be employed in the present invention are as follows. First, at least one substance having a capacity for stimulating the reticuloendothelial system is injected intravenously or intraperitoneally into a mammal (e.g. mouse, rabbit, guinea pig, etc.). As the substances having a capacity for stimulating the reticuloendothelial system, there are generally used Gram-positive bacteria, protozoas or yeasts, which are administered to the mammal in state of either of living microorganisms, dead microorganisms (e.g. after heat-treatment or formalin treatment) and microorganism cells extract. Examples of the Gram-positive bacteria include Propionibacteria such as *Propionibacterium acnes* (*Corynebacterium parvum*) and *Propionibacterium granulosum* (*Corynebacterium granulosum*), Mycobacteria such as bacillus Calmette-Guérin (BCG) and *Mycobacterium smegmatis*, and Nocardias such as *Nocardia erythropolis* and *Nocardia gardneri*. As a suitable protozoa, for example, Plasmodium or Toxoplasma is employable. As a suitable yeast, Zymosan extracted from *Saccharomyces cerevisiae* or others is generally used. There may also be employable synthetic high molecular compounds such as pyran copolymer. Second, 7 to 14 days after administration of the above-mentioned substance having a capacity for stimulating the reticuloendothelial system, endotoxin from a Gram-negative bacterium, for example, a lipopolysaccharide derived from *Escherichia coli, Pseudomonas aeruginosa,* or *Salmonella typhosa* is injected intravenously into said mammal. Third, 1.5 to 2 hours after the injection, body fluids (e.g. ascites, lymph, etc.) and/or serum or plasma of said mammal are taken or internal organs such as liver, spleen, etc. are homogenized and extracted with a physiological saline solution. These body fluids, serum, plasma and/or extract of internal organs may be employed as crude solution of TNF. Of them, however, serum or plasma is generally employed.

As mentioned above, the method for preparing TNF to be employed in the present invention is not limited to the above method. The method based on gene engineering and the tissue culture method in which cells having a TNF-producing capacity are employed can also be effectively utilized. It is to be noted that these methods are also applicable to production of human TNF as well.

The crude TNF produced by any of the methods as set forth above may be purified using the below-cited conventional biochemical techniques singly or in combination to give an aqueous purified TNF solution, which is lyophilized to give a purified TNF powder. As the suitable biochemical technique for purification of TNF, there can be mentioned, for example, a salting-out technique in which ammonium sulfate is employed, an ion exchange chromatography in which an anion exchange resin is employed, a gel filtration technique and an electrophoresis technique. As the purity of TNF is increased by practicing the above techniques for purification, it is recognized that the TNF gradually becomes instable. For example, a TNF sample so purified as to have a specific activity of 500,000 units/mg (the specific activity is expressed as units of TNF activity per mg of protein; the unit of TNF activity is defined later) is quite instable as seen from the data given in the Examples. Even the TNF samples having a specific activity lower than 500,000 units/mg also experience a decrease of the respective activity in some degree when they are in storage or subjected to freezing, thawing, lyophilization and other operations.

Accordingly, the present invention is directed to the stabilization of the TNF that has been purified to a high degree and has been rendered instable. The TNF to be stabilized according to the present invention may be either in the form of a solution or powder. However, it is preferred that the TNF to be stabilized be in the form of a solution.

It is preferred that the TNF solution to be stabilized according to the present invention constantly have a pH value of from 5 to 10, and, further, it is preferred that the solvent for the TNF solution to be stabilized be a suitable buffer. As the suitable buffer, there can be mentioned, for example, a phosphate buffer and a tris(hydroxymethyl)-aminomethane-HCl buffer. According to need, a salt, such as sodium chloride and potassium chloride, is added to the TNF solution. For example, a salt is added to the TNF solution so as to prepare an isotonic solution, when the TNF solution is used for injection. The purpose of addition of a salt is not limited to the above. The concentration of such a salt in the TNF solution may be determined, depending on the purpose of addition of the salt. For example, when the ultimate TNF solution is used for injection, an isotonic solution is prepared from the TNF solution by addition of sodium chloride up to a concentration of 0.15 M.

According to the method of the present invention, an effective amount of a stabilizing agent selected from a nonionic surfactant, at least one substance selected from the group consisting of D-glucose, D-galactose, D-xylose, D-glucuronic acid, a salt of D-glucuronic acid, trehalose, a dextran and a hydroxyethyl starch, and mixtures thereof is added to an aqueous solution or powder containing TNF.

The substance selected from the group consisting of D-glucose, D-galactose, D-xylose, D-glucuronic acid, a salt of D-glucuronic acid, trehalose, a dextran and a hydroxyethyl starch is hereinafter frequently referred to as "the sugar or sugar-related compounds".

As the suitable nonionic surfactant to be used in the present invention, there may be mentioned a polyoxyethylene fatty acid ester, a polyoxyethylene alkyl ether, a polyoxyethylene alkylphenyl ether, a polyoxyethylene sorbitan fatty acid ester, a polyoxyethylene glycerin fatty acid ester, a polyoxyethylene hydrogenated castor oil, a polyoxyethylene castor oil, a polyoxyethylene polyoxypropylene alkyl ether, a polyoxyethylene polyoxypropylene block polymer, a sorbitan fatty acid ester, a sucrose fatty acid ester, a glycerin fatty acid ester and the like. From the viewpoint of dispersibility or solubility, the nonionic surfactant having an HLB (Hydrophile Lipophile Balance) value of 9 to 20 is preferably used, and the nonionic surfactant having an HLB value of 13 to 18 is more preferably used in the present invention.

The HLB value of the nonionic surfactant to be used in the present invention may be measured according to various well-known methods, for example, the method as described in J. Soc. Cosmetic Chemists, 5,249 (1954).

As the polyoxyethylene fatty acid ester, preferred is a polyoxyethylene fatty acid ester having a saturated or unsaturated fatty acid residue with 8 to 20 carbon atoms in which the number of moles of added ethylene oxide (hereinafter referred to as "E.O.") is about 4 to 50. As such a polyoxyethylene fatty acid ester, there may be mentioned, for example, a polyoxyethylene stearate, a polyoxyethylene laurate and a polyoxyethylene oleate each having the number of moles of added E.O. of 4 to 50.

As the polyoxyethylene alkyl ether, preferred is a polyoxyethylene alkyl ether having a saturated or unsaturated alkyl group with 8 to 20 carbon atoms in which the number of moles of added E.O. is about 5 to 55. As such a polyoxyethylene alkyl ether, there may be mentioned, for example, a polyoxyethylene lauryl ether, a polyoxyethylene cetyl ether, a polyoxyethylene stearyl ether and a polyoxyethylene oleyl ether each having the number of moles of added E.O. of 5 to 55.

As the polyoxyethylene alkylphenyl ether, preferred is a polyoxyethylene alkylphenyl ether having a saturated or unsaturated alkyl group with 5 to 10 carbon atoms in which the number of moles of added E.O. is about 5 to 55. As such a polyoxyethylene alkylphenyl ether, there may be mentioned, for example, a polyoxyethylene octylphenyl ether and a polyoxyethylene nonylphenyl ether each having the number of moles of added E.O. of about 5 to 55.

As the polyoxyethylene sorbitan fatty acid ester, preferred is a polyoxyethylene sorbitan fatty acid ester having a saturated or unsaturated fatty acid residue with 8 to 20 carbon atoms in which the number of moles added E.O. is about 5 to 50. As such a polyoxyethylene sorbitan fatty acid ester, there may be mentioned, for example, a polyoxyethylene sorbitan monolaurate, a polyoxyethylene sorbitan monopalmitate, a polyoxyethylene sorbitan monostearate, a polyoxyethylene sorbitan monooleate, and a polyoxyethylene sorbitan tristearate each having the number of moles of added E.O. of about 5 to 50.

As the polyoxyethylene glycerin fatty acid ester, preferred is a polyoxyethylene glycerin fatty acid ester having a saturated or unsaturated fatty acid residue with 8 to 20 carbon atoms in which the number of moles of added E.O. is about 5 to 50. As such a polyoxyethylene glycerin fatty acid ester, there may be mentioned, for example, a polyoxyethylene glyceryl monostearate, and a polyoxyethylene glyceryl monooleate each having the number of moles of added E.O. of about 5 to 50.

As the polyoxyethylene hydrogenated castor oil and polyoxyethylene castor oil, preferred is a polyoxyethylene hydrogenated castor oil and polyoxyethylene castor oil each having the number of moles of added E.O. of about 20 to 150.

As the polyoxyethylene polyoxypropylene alkyl ether, preferred is a polyoxyethylene polyoxypropylene alkyl ether having a saturated or unsaturated alkyl group with 12 to 18 carbon atoms and having an E.O. content of about 65 to 85% by weight. As such a polyoxyethylene polyoxypropylene alkyl ether, there may be mentioned, for example, the polyoxyethylene polyoxypropylene cetyl ether having an E.O. content of about 65 to 85% by weight.

As the polyoxyethylene polyoxypropylene block polymer, preferred is a polyoxyethylene polyoxypropylene block polymer having a number average molecular weight of about 3,000 to 15,000 and having an E.O. content of about 65 to 85% by weight.

As the sorbitan fatty acid ester, preferred is a mono- or sesqui-acid ester of a sorbitan with a saturated or unsaturated fatty acid having 8 to 20 carbon atoms. As such a sorbitan fatty acid ester, there may be mentioned, for example, a sorbitan monolaurate, a sorbitan monopalmitate, and a sorbitan sesquioleate.

As the sucrose fatty acid ester, preferred is a monoacid ester of sucrose with a saturated or unsaturated fatty acid having 8 to 20 carbon atoms. As such a sucrose fatty acid ester, there may be mentioned, for example, a sucrose monopalmitate, and a sucrose monostearate.

As the glycerin fatty acid ester, preferred is a monoacid ester of glycerin with a saturated or unsaturated fatty acid having 8 to 20 carbon atoms. As such a glycerin fatty acid ester, there can be mentioned, for example, a glyceryl monostearate, and a glyceryl monooleate.

Among the above-mentioned nonionic surfactant, a polyoxyethylene sorbitan fatty acid ester, a polyoxyethylene hydrogenated castor oil, a polyoxyethylene castor oil and a polyoxyethylene polyoxypropylene block polymer as defined above are more preferably employed because they are relatively low in toxicity. A polyoxyethylene sorbitan monooleate (the number of moles of added E.O.: 20) [hereinafter referred to as "polyoxyethylene (20) sorbitan monooleate" and other nonionic surfactants are hereinafter indicated in the same manner], a polyoxyethylene (60) hydrogenated castor oil and a polyoxyethylene polyoxypropylene block polymer having a number average molecular weight of about 8,350 and having an E.O. content of 80% by weight are most preferable.

The above-mentioned nonionic surfactants may be used alone or in combination.

As mentioned above, as the sugar or sugar-related compounds there may be mentioned at least one substance selected from the group consisting of D-glucose, D-galactose, D-xylose, D-glucuronic acid, a salt of D-glucuronic acid, trehalose, a dextran and a hydroxyethyl starch.

As the salt of D-glucuronic acid, there may be mentioned an alkali metal salt such as sodium salt and potassium salt, and an alkaline earth metal salt such as calcium salt and magnesium salt.

As the hydroxyethyl starch, there may be used a hydroxyethyl starch having an average molecular weight of 30,000 to 400,000, preferably 200,000.

As the dextran, preferred is a dextran having an average molecular weight of 10,000 to 80,000. As such a dextran, there may be mentioned Dextran 10, Dextran 40 and Dextran 70 respectively having average molecular weights of 10,000, 40,000 and 70,000.

Among the sugar or sugar-related compounds, trehalose is most preferable.

The above-mentioned sugar or sugar-related compounds may be used alone or in combination.

Further, in the present invention, there may also be used derivatives of D-glucose, D-galactose, D-xylose, D-glucuronic acid and trehalose such as phosphate ester or its salt, methyl ether and methyl glycoside, because they have a TNF stabilizing effect.

The nonionic surfactant to be employed in the present invention is added in an amount of about 1 $\mu$g to 1 mg, preferably about 5 $\mu$g to 100 $\mu$g, especially preferably about 10 $\mu$g to 100 $\mu$g, per ml of the TNF solution having a TNF activity of $10^2$ to $10^9$ units/ml (the unit of activity is defined later). The way in which the nonionic surfactant is added is not critical. For example, the nonionic surfactant may be directly added to the TNF solution. Alternatively, the nonionic surfactant may be dissolved, in advance, in water or a suitable buffer or organic solvent such as ethanol, and added to the TNF solution. Addition of the nonionic surfactant may be effected at any time during the purification step or the step of manufacturing pharmaceutical preparations.

When two or more different kinds of nonionic surfactants are employed, they are added in such an amount that the total amount thereof falls within the amount range as defined above.

The sugar or sugar-related compounds to be employed in the present invention are added in an amount of about 10 mg or more, preferably 100 mg or more, per ml of the TNF solution having a TNF activity of $10^2$ to $10^9$ units/ml. The upper limit of the amount of the sugar or sugar-related compounds are usually determined from the viewpoints of the solubility of the sugar or sugar-related compounds and viscosity of the resulting solution and from the economical viewpoint. The upper limit of the amount of the sugar or sugar-related compounds are generally 500 mg, per ml of the TNF solution. When the TNF to be stabilized is in a powdery form, the sugar or sugar-related compounds are added in such an amount as will cause an aqueous solution, which is obtained by dissolving the powdery TNF to exhibit an activity of $10^2$ to $10^9$ units/ml, to have the above-mentioned concentrations of the sugar or sugar-related compounds.

The way in which the sugar or sugar-related compounds are added is not critical. For example, the sugar or sugar-related compounds in a powdery form may be directly added to the TNF solution. Alternatively, the powder of the sugar or sugar-related compounds may be dissolved, in advnace, in water or a suitable buffer, and added to the TNF solution. Further, alternatively, the powder of the sugar or sugar-related compounds may be mixed with the TNF powder. Addition of the sugar or sugar-related compounds may be effected at any time during the purification step or the step of manufacturing pharmaceutical preparations.

When two or more different kinds of sugars or sugar-related compounds are employed, they are added in such an amount that the total amount thereof falls within the amount range as defined above.

The nonionic surfactant and the sugar or sugar-related compounds to be used in the present invention may be used in combination. In such a case, the nonionic surfactant and the sugar or sugar-related compounds may be added in such amounts as fall within the above-defined amount ranges, respectively.

It is preferred that storing and purification of and manufacturing pharmaceutical preparations from the TNF solution in which a stabilizing agent to be employed according to the present invention is incorporated, if kept in the form of a solution, be performed at a temperature of from 0° to 30° C., more preferably from 0° to 10° C. When the TNF solution is stored in a frozen form, it is preferred that the temperature for storage be maintained below 0° C., more preferably below $-20°$ C.

The TNF solution in which an effective amount of at least one stabilizing agent, according to the present invention, is incorporated does maintain its TNF activity during the storing, whether it is in the form of a solution or in a frozen form, or during the steps of purification and manufacturing pharmaceutical preparations.

Further, the method for stabilizing TNF, according to the present invention, is also applicable to lyophilization. Illustratively stated, when TNF solutions (especially, in the case of highly purified TNF) are subjected to lyophilization, the activities thereof generally markedly drop. However, TNF solutions containing an effective amount of at least one stabilizing agent, according to the present invention, are lyophilized with retaining about 50% or more of its activity to give a TNF powder. The TNF powder may be dissolved to give a stable aqueous TNF solution in which the concentrations of the stabilizing agent and TNF fall within the range as defined above. The stabilizing agent as defined in the present invention may, alternatively, be incorporated in the lyophilized TNF preparations. When TNF is stored in a powdery form, it is preferred that the temperature for storage be maintained at 25° C. or below.

To assay the activity of TNF, there are usually employed two methods, i.e. the in vivo method in which the tumor necrosis effect is measured in vivo, and the in vitro method in which the cytotoxic effect on neoplastic cells is measured in vitro.

As the in vivo method, there can be mentioned, for example, the method of Carswell et al. [see Proc. Nat. Acad. Sci. USA, 72(9), 3666–3670 (1975)]. According to this method, BALB/c sarcoma Meth-A cells ($2 \times 10^5$ cells) are transplanted intradermally at armpit of each of (BALB/c x C57BL/6)F$_1$ mice and, 7 days later, mice with tumors of 7–8 mm in diameter, good vascularization and no spontaneous central necrosis are selected for evaluation. A TNF sample (0.5 ml) diluted with a physiological saline solution is injected through the tail vein of each of the mice. The activity of the TNF sample is evaluated after 24 hours according to the following criterion.

(−): no change (+): slight hemorrhagic necrosis
(++): moderate hemorrhagic necrosis (central necrosis extending over approximately 50% of the tumor surface)
(+++): marked hemorrhagic necrosis (massive necrosis leaving a small viable rim along the tumor periphery)

As the in vitro method for the assay of TNF activity, there can be mentioned, for example, the method of Ruff et al. [see Lymphokines, Vol. 2, edited by E. Pick, Academic Press, N.Y., 245–248 (1981)] and the method of Kull et al. [see J. Immunol., 126 (4), 1279–1283 (1981)].

The in vitro method that the present inventors have employed for the assay of TNF activity has been developed by improving the above-mentioned conventional methods. The in vitro method of the present inventors, in which the cytotoxic activity of TNF against L-M cells (American Type Culture Collection CCL 1.2) is measured, is carried out as follows. As culture vessels, there are employed 96-well microtiter plates produced by Flow Laboratories, Inc. (U.S.A.), and L-M cells are cultured in Eagle's minimum essential medium [see Science, 130, 432–437 (1959)] containing 10 v/v% heat-inactivated fetal calf serum. A TNF sample (0.1 ml) serially diluted with the medium and the L-M cell suspension (0.1 ml, $1\times10^4$ cells) are mixed in each well of the plates and the plates are incubated at 37° C. for 48 hours in an air containing 5% carbon dioxide. At the end of the culture period, a 20% aqueous solution of glutaraldehyde (20 μl) is added to fix the cells. After fixation, the plates are washed with distilled water and allowed to dry, and 0.05% methylene blue (0.1 ml) is added to stain the viable cells. The plates are thoroughly washed with distilled water to remove excess dye and allowed to dry. 3% Hydrochloric acid (0.2 ml) is added to each well to extract the dye from stained cells. Absorbance of each well at 665 nm is measured with Titertek Multiskan produced by Flow Laboratories, Inc. The absorbance is proportional to the number of viable cells. The TNF activity, unit(U)/ml, is defined as the reciprocal dilution of TNF that causes 50% cytotoxicity, and can be obtained by plotting the dilution versus the absorbance on a graph. All the TNF activities, assayed according to the in vitro method, as used hereinafter are expressed by the above-defined unit.

According to the method of the present invention, efficient and steady supply, on a commercial scale, of highly purified TNF, which is believed to be a clinically applicable effective antitumor medicine, can be ensured because in the method of the present invention, the activity of TNF is maintained during the storing, whether TNF is in the form of a solution, a frozen mass or a lyophilized preparation, and during the steps of purification and manufacturing pharmaceutical preparations. It has also been found that the TNF solution or powder, in which a stabilizing agent selected from a nonionic surfactant, at least one substance selected from the group consisting of D-glucose, D-galactose, D-xylose, D-glucuronic acid, a salt of D-glucuronic acid, trehalose, a dextran and a hydroxyethyl starch, and mixtures thereof is incorporated, can be safely administered to the human body because the present stabilizing agent lacks the antigenicity in human, wherefore the novel composition of the present invention is especially useful when TNF is clinically applied as an antitumor medicine.

Further, it should be noted that the stabilizing agent to be used in the present invention does not interfere with the measurement of the purity of TNF and, therefore, when the stabilizing agent to be used in the present invention is incorporated in an aqueous solution or powder containing TNF, the purity of TNF in the aqueous solution or powder can be exactly determined.

Moreover, the stabilizing agent to be used in the present invention can be obtained with high quality, at reasonable cost.

The present invention will now be described in more detail with reference to the following Referential Example, Working Examples and Comparative Examples that by no means limit the scope of the invention.

REFERENTIAL EXAMPLE

Female rabbits, each weighing from 2 to 3 kg, were each injected intravenously with 75 mg of formalin-killed cells of *Propionibacterium acnes* (*Corynebacterium parvum;* Wellcome Research Laboratories, England). Eight days later, the rabbits were each injected intravenously with 100 μg of endotoxin (lipopolysaccharide from *Escherichia coli* 026:B6, produced by Difco Laboratories, U.S.A.). The blood was obtained from each rabbit by cardiac puncture 2 hours after the injection of endotoxin, and the blood obtained was mixed with a small amount of heparin. The blood was centrifuged at 3,000 rpm for 15 minutes. As a result, a plasma having a TNF activity of 2,500 U/ml was obtained.

The thus obtained plasma (10 liters) containing TNF was diluted with 5 liters of 0.03 M phosphate buffer (pH 7.8). The diluted plasma was applied to a column (10 ×42 cm) of DEAE-Sepharose CL-6B (manufactured and sold by Pharmacia Fine Chemicals AB, Sweden) equilibrated with 0.03 M phosphate buffer (pH 7.8) containing 0.13 M NaCl. The column was washed with 2.5 liters of 0.03 M phosphate buffer (pH 7.8) containing 0.13 M NaCl, and the adsorbed TNF was eluted with a linear NaCl gradient consisting of 5.0 liters of 0.03 M phosphate buffer (pH 7.8) containing 0.15 M NaCl and 5.0 liters of 0.03 M phosphate buffer (pH 7.8) containing 0.3 M NaCl. The flow rate was 230 ml/hour and 45-ml fractions were collected. TNF activity was found in the fractions eluted with 0.20–0.24 M NaCl. The fractions with TNF activity were pooled and dialyzed overnight against 0.03 M Tris-HCl buffer (pH 7.2) containing 0.13 M NaCl.

The dialyzed TNF solution was rechromatographed on the DEAE-Sepharose CL-6B column (3.0×30 cm) equilibrated with 0.03 M Tris-HCl buffer (pH 7.2) containing 0.15 M NaCl. The adsorbed TNF was eluted with a linear NaCl gradient consisting of 500 ml of the equilibrating buffer and 500 ml of 0.03 M Tris-HCl buffer (pH 7.8) containing 0.3 M NaCl. The flow rate was 40 ml/hour, and 10-ml fractions were collected. The fractions with TNF activity were pooled and concentrated.

The concentrate was gel-filtered through the column (5×100 cm) of Sephacryl S-200 (manufactured and sold by Pharmacia) equilibrated with 5 mM phosphate buffer (pH 7.0) containing 0.15 M NaCl. The elution was performed with the equilibrating buffer. The flow rate was 80 ml/hour, and 13-ml fractions were collected. The fractions with TNF activity were pooled and concentrated by ultra-filtration.

The TNF solution thus obtained was found to have a specific activity of $5.0\times10^5$ U/mg-protein and have a purity 10,000-fold higher than that of the plasma.

The thus obtained TNF solution was subjected to rechromatography on the same column (Sephacryl S-200) using the same buffer, thereby to obtain a TNF solution having a specific activity of $1.0 \times 10^6$ U/mg-protein.

EXAMPLE 1

Rabbit TNF, having a specific activity of $5.0 \times 10^5$ U/mg, obtained according to the procedures as described in the Referential Example was diluted with 0.1 M phosphate buffer (pH 7.0) containing 0.15 M sodium chloride to obtain a TNF solution having a TNF activity of 1,000 U/ml. To aliquots of the thus obtained TNF solution, various nonionic surfactants as indicated in Table 1 were separately added as the stabilizing agent in such an amount as will cause the resulting solution to have a concentration of 10 μg/ml.

For each of the resulting solutions, the remaining activity was determined with respect to (i) the samples respectively subjected to storing for 2 days, 7 days and 30 days at 4° C., (ii) the samples respectively subjected to one cycle and three cycles of freezing (−70° C.) and thawing, and (iii) the sample subjected to freezing at −70° C., lyophilization and storing for 7 days at 25° C. In carrying out the above test, the TNF solution in which no stabilizing agent was incorporated was used as control. With respect to the lyophilized preparation [see (iii) above], it was dissolved in sterile distilled water and then subjected to assay of the TNF activity.

To determine the remaining activity, the activity of each sample was assayed in vitro or in vivo, according to the methods as described hereinbefore. In the in vitro method, the remaining activity (%) was calculated from the assay value according to the following equation:

$$\text{Remaining activity (\%)} = A/B \times 100$$

wherein A is the TNF activity of the sample after storing or physical treatment and B is the TNF activity of the sample before storing or physical treatment.

In the in vivo method, each sample solution was concentrated to have a concentration 30 times that at start by means of the Mini-Module NM-3 (trade mark of the ultrafiltration equipment manufactured and sold by Asahi Chemical Industry Co. Ltd., Japan). Then, 0.5 ml of each of the thus concentrated TNF solutions was injected, through the tail vein, into each of a group of five tumor-bearing mice. The TNF activity was assayed 24 hours later in accordance with the criterion as described hereinbefore. The results obtained are shown in Table 1.

EXAMPLE 2

To aliquots of the TNF solution having the same TNF activity as that employed in Example 1, various sugars and sugar-related compounds as indicated in Table 2 were separately added as the stabilizing agent to form two different solutions respectively having a concentration of 100 mg/ml and a concentration of 300 mg/ml. The stabilizing effect of the sugars and sugar-related compounds was evaluated in the same manner as in Example 1. However, the sample solution to which the dextran or hydroxyethyl starch was added could not be concentrated to one thirtieth of its original volume and hence its TNF activity was not assayed by the in vivo method. The results obtained are shown in Table 2.

TABLE 1

Stabilizing effect of nonionic surfactants

| Condition | Control (before storing or physical treatment) | | Storing at 4° C. (Solution) | | | | Freezing-thawing | | Storing at 25° C. (lyophilized preparation) |
|---|---|---|---|---|---|---|---|---|---|
| Assay method of activity | in vitro | in vivo | in vitro days | | | in vivo days | in vitro repetition | | in vitro days |
| Stabilizing agent (trademark or trivial name) | | | 2 | 7 | 30 | 7 | 1 | 3 | 7 |
| Control (without stabilizing agent) | 100 | +++4,++1 | 5 | <3 | <3 | −5 | 9 | 4 | 5 |
| POE (4) laurate (Nissan Nonion L-4) | 100 | +++5 | 93 | 90 | 80 | +++3,++1,+1 | 56 | 60 | 57 |
| POE (6) stearate (Nissan Nonion S-6) | 100 | +++4,++1 | 90 | 99 | 85 | +++2,++1,+2 | 60 | 72 | 57 |
| POE (6) oleate (Nissan Nonion O-6) | 100 | +++3,++2 | 85 | 97 | 85 | +++2,++1,+2 | 41 | 63 | 56 |
| POE (20) lauryl ether (Nissan Nonion K-220) | 100 | +++3,++2 | 95 | 95 | 93 | +++3,++1, +1 | 48 | 48 | 50 |
| POE (23) lauryl ether (Brij 35) | 100 | +++4,++1 | 90 | 95 | 92 | +++2,++2,+1 | 55 | 75 | 59 |
| POE (20) cetyl ether (Brij 58) | 100 | +++4,++1 | 91 | 90 | 90 | +++3,++1,+1 | 43 | 60 | 55 |
| POE (20) stearyl ether (Nissan Nonion S-220) | 100 | +++2,++1,+2 | 99 | 97 | 90 | +++2,++2,+1 | 59 | 40 | 51 |
| POE (15) oleyl ether (Nissan Nonion E-215) | 100 | +++4,++1 | 90 | 93 | 82 | +++3,++1,+1 | 67 | 52 | 60 |
| POE (9–10) octylphenyl ether (Triton X-100) | 100 | +++4,++1 | 71 | 96 | 85 | +++3,++1,+1 | 58 | 60 | 59 |
| POE (10) nonylphenyl ether (Nissan Nonion NS-210) | 100 | +++3,++2 | 95 | 88 | 80 | +++3,++1,+1 | 69 | 45 | 57 |
| Sorbitan monopalmitate (NIKKOL SP-10) | 100 | +++3,++2 | 98 | 90 | 95 | +++2,++1,+2 | 63 | 32 | 61 |
| Sorbitan sesquioleate (NIKKOL SO-15) | 100 | +++4, ++1 | 90 | 95 | 90 | +++3,++1,+1 | 47 | 40 | 50 |
| POE (20) sorbitan monolaurate (Tween 20) | 100 | +++4, ++1 | 97 | 96 | 84 | +++2,++2,+1 | 44 | 50 | 52 |
| POE (20) sorbitan monostearate (Tween 60) | 100 | +++4,++1 | 97 | 96 | 95 | +++2,++2,+1 | 66 | 70 | 61 |
| POE (20) sorbitan monooleate (Tween 80) | 100 | +++3,++2 | 99 | 98 | 100 | +++4,++1 | 88 | 74 | 68 |
| POE (20) sorbitan tristearate (Tween 85) | 100 | +++4,++1 | 95 | 92 | 90 | +++2,++2,+1 | 78 | 82 | 57 |
| POE (60) hydrogenated castor oil (NIKKOL HCO-60) | 100 | +++4,++1 | 92 | 97 | 98 | +++5 | 70 | 62 | 69 |
| POE (40) castor oil (NIKKOL | 100 | +++3,++2 | 90 | 100 | 92 | +++3,++2 | 60 | 65 | 63 |

TABLE 1-continued

Stabilizing effect of nonionic surfactants

| Condition<br>Assay method of activity<br>Stabilizing agent<br>(trademark or trivial name) | Control<br>(before storing or<br>physical treatment) | | Storing at 4° C.<br>(Solution) | | | | Freezing-<br>thawing | | Storing at 25° C.<br>(lyophilized<br>preparation) |
|---|---|---|---|---|---|---|---|---|---|
| | in vitro | in vivo | in vitro<br>days | | in vivo<br>days | | in vitro<br>repetition | | in vitro<br>days |
| | | | 2 | 7 | 30 | 7 | 1 | 3 | 7 |
| CO-40TX)<br>POE polyoxypropylene block polymer<br>(Pluronic F68) | 100 | +++4,++1 | 99 | 98 | 95 | +++5 | 75 | 53 | 69 |

Note:
The figures in the column marked "in vitro" represent the remaining activity as defined hereinbefore.
The figures in the columns marked "in vivo" represent the number of mice. The meaning of symbols (−, +, ++, etc.) is given hereinbefore.
POE: the abbreviation of "polyoxyethylene"
Nissan Nonion: the trademark of the nonionic surfactants produced by Nippon Oil And Fats Co., Ltd., Japan
NIKKOL: the trademark of the surfactants produced by Nikko Chemicals Co., Ltd., Japan
Briji, Tween, Triton and Pluronic: the trivial name of the nonionic surfactants
The nonionic surfactants in the table which have the trivial name of Briji or Tween are the products of Wako Pure Chemical Industries, Ltd., Japan.
The Triton X-100 in the table is the product of Rohm & Haas Co., U.S.A.
The Pluronic F68 in the table is the product of Asahi Denka Kogyo K.K., Japan.

EXAMPLE 3

TABLE 2

| Condition<br>Assay method of activity<br>Stabilizing agent | Concentration<br>(mg/ml) | Control<br>(before storing or<br>physical treatment) | | Storing at 4° C.<br>(Solution) | | | | Freezing-<br>thawing | | Storing at 25° C.<br>(lyophilized<br>preparation) |
|---|---|---|---|---|---|---|---|---|---|---|
| | | in vitro | in vivo | in vitro<br>days | | in vivo<br>days | | in vitro<br>repetition | | in vitro<br>days |
| | | | | 2 | 7 | 30 | 7 | 1 | 3 | 7 |
| Control (without stabilizing agent) | — | 100 | +++4,++1 | 5 | <3 | <3 | −5 | 9 | 4 | 5 |
| D-Glucose | 100 | 100 | +++3,++2 | 75 | 90 | 66 | +++2,++2,+1 | 54 | 37 | 51 |
| | 300 | 100 | +++4,++1 | 84 | 91 | 86 | +++3,++1,+1 | 88 | 82 | 65 |
| D-Galactose | 100 | 100 | +++4,++1 | 88 | 68 | 35 | +++1,++2,+2 | 45 | 36 | 48 |
| | 300 | 100 | +++4,+1 | 74 | 80 | 75 | +++2,++3 | 76 | 57 | 60 |
| D-Xylose | 100 | 100 | +++3,++2 | 62 | 51 | 24 | +++1,+4 | 50 | 36 | 47 |
| | 300 | 100 | +++4,++1 | 79 | 70 | 50 | +++1,++2,+2 | 82 | 70 | 61 |
| D-Glucuronic acid (Na) | 100 | 100 | +++5 | 82 | 77 | 72 | +++2,++2,+1 | 57 | 35 | 54 |
| | 300 | 100 | +++4,++1 | 87 | 93 | 97 | +++4,+1 | 58 | 47 | 54 |
| Trehalose | 100 | 100 | +++4,++1 | 100 | 97 | 91 | +++4,++1 | 81 | 56 | 82 |
| | 300 | 100 | +++3,++2 | 100 | 86 | 100 | +++4,++1 | 91 | 84 | 90 |
| Dextran 10 | 100 | 100 | — | 78 | 60 | 23 | — | 46 | 36 | 53 |
| | 300 | 100 | — | 100 | 83 | 53 | — | 65 | 83 | 67 |
| Dextran 70 | 100 | 100 | — | 62 | 50 | 15 | — | 69 | 46 | 62 |
| | 300 | 100 | — | 73 | 65 | 27 | — | 71 | 69 | 64 |
| Hydroxyethyl starch | 100 | 100 | — | 96 | 58 | 42 | — | 75 | 49 | 54 |
| | 300 | 100 | — | 86 | 69 | 43 | — | 70 | 57 | 61 |

Note:
The figures in the columns marked "in vitro" represent the remaining activity as defined hereinbefore.
The figures in the columns marked "in vivo" represent the number of mice. The meaning of symbols (−, +, ++, etc.) is given hereinbefore.
The average molecular weight of the hydroxyethyl starch is about 200,000.

Figure 2:
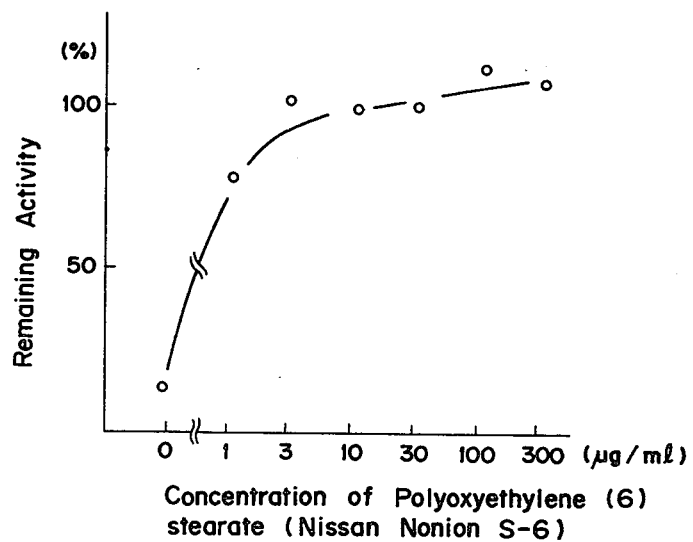
FIG. 2 is a graph showing the effect of the concentration of polyoxyethylene (6) stearate (Nissan Nonion S-6) on the remaining activity of TNF after storage at 4° C. for 7 days.
Figure 3:
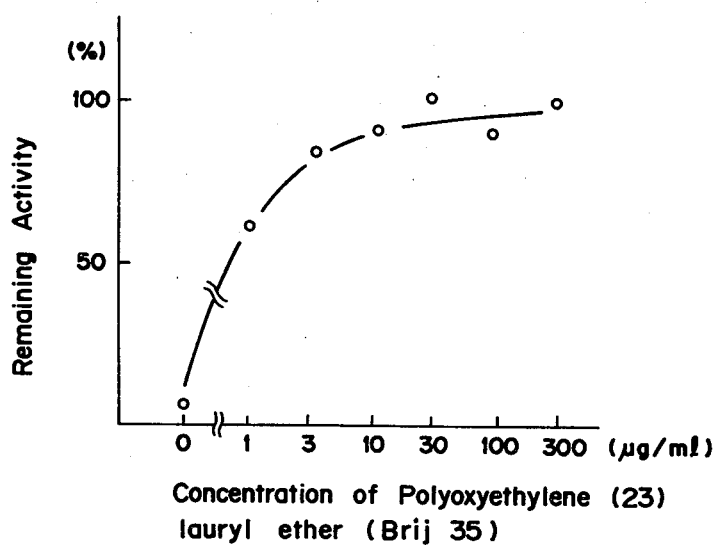
FIG. 3 is a graph showing the effect of the concentration of polyoxyethylene (23) lauryl ether (Brij 35) on the remaining activity of TNF after storage at 4° C. for 7 days.
Figure 4:
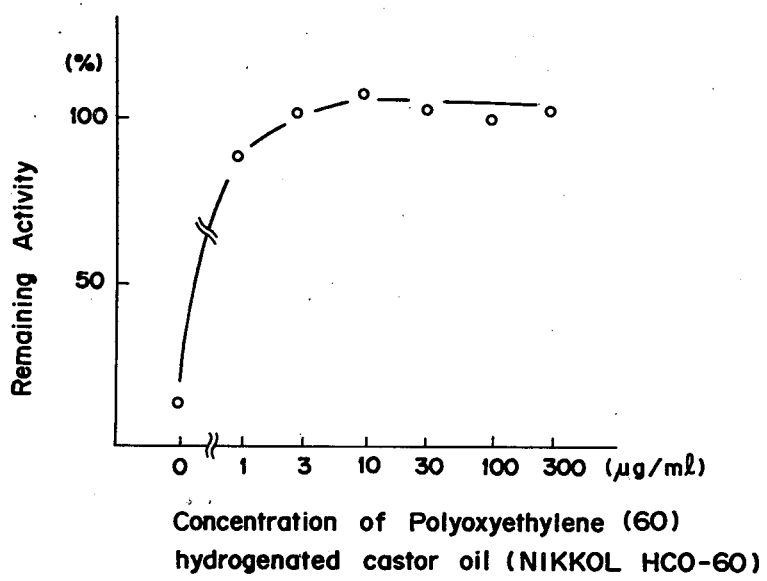
FIG. 4 is a graph showing the effect of the concentration of polyoxyethylene (60) hydrogenated castor oil (NIKKOL HCO-60) on the remaining activity of TNF after storage at 4° C. for 7 days.
Figure 5:
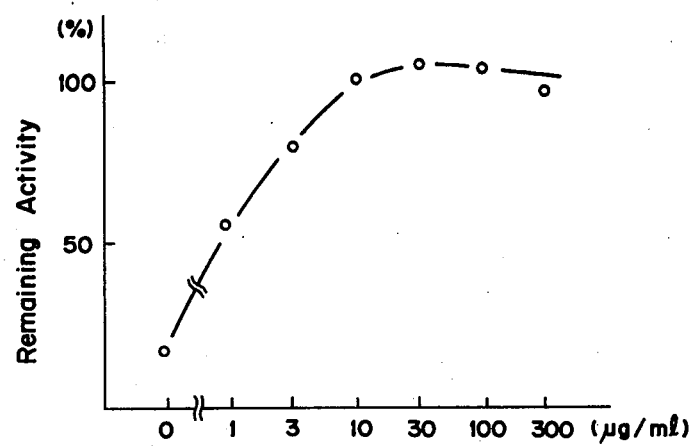
FIG. 5 is a graph showing the effect of the concentration of polyoxyethylene polyoxypropylene block polymer (Pluronic F68) on the remaining activity of TNF after storage at 4° C. for 7 days.
Figure 6:
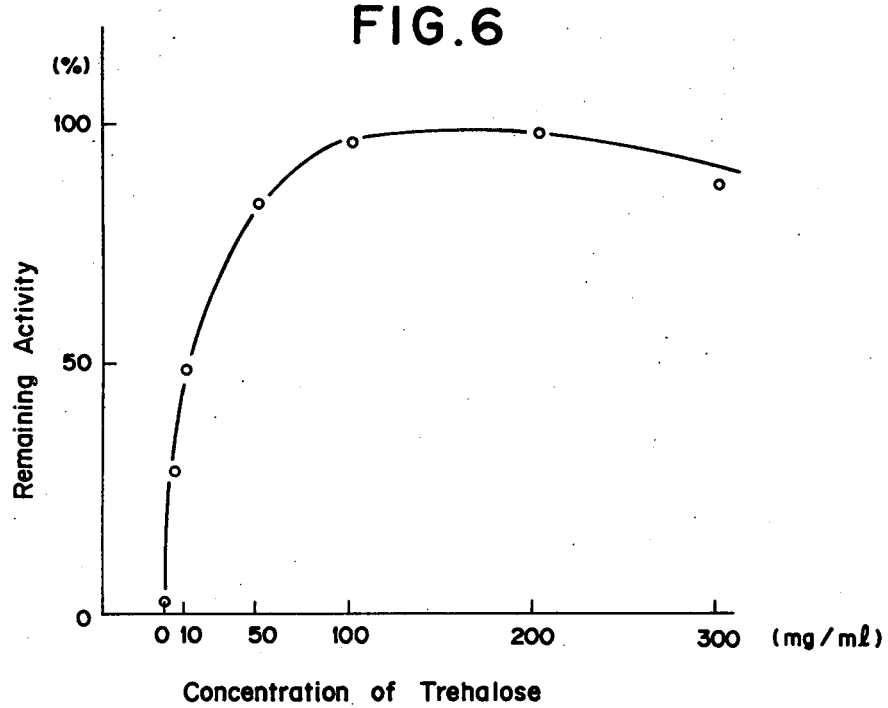
FIG. 6 is a graph showing the effect of the concentration of trehalose on the remaining activity of TNF after storage at 4° C. for 7 days.

To aliquots of the TNF solution having the same TNF activity as that employed in Example 1, each of polyoxyethylene (20) sorbitan monooleate (Tween 80, the product of Wako Pure Chemical Industries, Ltd., Japan), polyoxyethylene (6) stearate (Nissan Nonion S-6, the product of Nippon Oil And Fats Co., Ltd., Japan), polyoxyethylene (23) lauryl ether (Brij 35, the product of Wako Pure Chemical Industries, Ltd.), polyoxyethylene (60) hydrogenated castor oil (NIKKOL HCO-60, the product of Nikko Chemicals Co., Ltd., Japan), polyoxyethylene polyoxypropylene block polymer (number average molecular weight: about 8350, E.O. content: 80%) (Pluronic F68, the product of Asahi Denka Kogyo K.K., Japan) and trehalose was separately added as the stabilizing agent at varied concentrations. Each of the resulting solutions was stored at 4° C. for 7 days, and then subjected to the assay of the TNF activity according to the in vitro method. The remaining TNF activity (%) was calculated in the same manner as in Example 1. The results obtained are shown in FIGS. 1 to 6.

EXAMPLE 4

Rabbit TNF, having a specific activity of $1.0 \times 10^6$ U/mg, obtained according to the procedures described in the Referential Example was diluted with 0.1 M phosphate buffer (pH 7.0) containing 0.15 M sodium chloride, whereby TNF solutions respectively having TNF activities of 100 U/ml, 1,000 U/ml, 10,000 U/ml and 100,000 U/ml were prepared. To an aliquot of each of the thus prepared TNF solutions, NIKKOL HCO-60 and trehalose were separately added in such an amount as will cause the resulting solution to have a concentration of 10 μg/ml and 100 mg/ml, respectively. Each of the resulting TNF solutions was stored at 4° C. for 7 days, and subjected to the assay of the TNF activity according to the in vitro assay method. The remaining TNF activity (%) was calculated in the same manner as in Example 1. As control, another aliquot of each of the TNF solutions in which neither NIKKOL HCO-60 nor trehalose was incorporated was also subjected to the assay of the TNF activity. The results obtained are shown in Table 3.

TABLE 3

Stabilizing effect of NIKKOL HCO-60 and trehalose

| Concentration of TNF, U/ml | 0 (control) | NIKKOL HCO-60 10 μg/ml | Trehalose 100 mg/ml |
|---|---|---|---|
| 100 | 3 | 86 | 79 |
| 1,000 | 5 | 99 | 96 |
| 10,000 | 43 | 98 | 101 |
| 100,000 | 47 | 101 | 98 |

[The figures represent the remaining activity of TNF (%).]

COMPARATIVE EXAMPLE 1

The TNF stabilizing effect and cytotoxic activity of various surfactants and alcohols were examined. As nonionic surfactants, polyoxyethylene (20) sorbitan monoolate (Tween 80), polyoxyethylene (60) hydrogenated castor oil (NIKKOL HCO-60) and polyoxyethylene polyoxypropylene block polymer (Pluronic F68) were employed. As comparative additives, sodium dodecyl sulfate (an anionic surfactant), cetyltrimethylammonium bromide (a cationic surfactant) and various alcohols as indicated in Table 4 (which are well-known stabilizing agents for the solutions of customary physiologically active substances) were employed.

The TNF stabilizing effect and cytotoxic activity of the above-mentioned additives were examined according to the following methods.

(i) Stabilizing effect:

To aliquots of the same TNF solution as that employed in Example 1, the above-mentioned surfactants and alcohols were respectively added in varied concentrations (0.05 mg/ml and 0.5 mg/ml in the case of surfactants; 5 mg/ml in the case of ethanol; and 100 mg/ml in the case of the other alcohols). Subsequently, the remaining TNF activity (%) with respect to each solution was determined in the same manner as in Example 1.

(ii) Cytotoxic activity:

The TNF solutions having the same additive concentrations as indicated in item i) above were prepared, followed by 100-time dilution with Eagle's minimum essential medium as mentioned before. Subsequently, the cytotoxic activity of each of the diluted solutions was assayed in the same manner as described before with respect to the assay of the TNF activity according to the in vitro assay method. In the abovementioned assay, the cytotoxic activity was evaluated according to the following criterion.

+ (cytotoxic): lethality of 50% or more of the L-M cells
− (non-cytotoxic): lethality of less than 50% of the L-M cells The results obtained are shown in Table 4 below.

TABLE 4

| Condition | | | Storing at 4° C. | | | | | |
|---|---|---|---|---|---|---|---|---|
| Assay method of activity | | | in vitro | | | | in vivo | |
| Additive | Concentration | Cytotoxic | days | | | | days | |
| (trademark or trivial name) | (mg/ml) | activity | 0 | 2 | 7 | 30 | 0 | 7 |
| Control (without stabilizing agent) | — | — | 100 | 5 | <3 | <3 | +++4,++1 | −5 |
| POE (20) sorbitan monostealate (Tween 80) | 0.05 | — | 100 | 100 | 96 | 95 | +++4,++1 | +++3,++2 |
|  | 0.5 | — | 100 | 100 | 100 | 98 | +++5 | +++4,+1 |
| POE (60) hydrogenated castor oil (NIKKOL HCO-60) | 0.05 | — | 100 | 97 | 100 | 98 | +++3,++2 | +++3,++2 |
|  | 0.5 | — | 100 | 98 | 96 | 98 | +++4,++1 | +++3,++2 |
| POE polypropylene block polymer (Pluronic F68) | 0.05 | — | 100 | 99 | 91 | 85 | +++4,++1 | +++5 |
|  | 0.5 | — | 100 | 97 | 100 | 95 | +++5 | +++3,++2 |
| Sodium dodecyl sulfate | 0.05 | — | 100 | 60 | 8 | <3 | +++4,++1 | +1,−4 |
|  | 0.5 | + | * | * | * | * | +++3,++1 | −4, dead 1 |
| Cetyltrimethylammonium bromide | 0.05 | + | * | * | * | * | +++2,++2,+1 | −4, dead 1 |
|  | 0.5 | + | * | * | * | * | +++3,++2 | −2, dead 3 |
| Polyethylene glycol | | | | | | | | |
| 1500 | 100 | — | 100 | 7 | <3 | <3 | +++4,++1 | −5 |
| 6000 | 100 | — | 100 | 52 | <3 | <3 | +++3,++2 | +1,−4 |
| Sorbitol | 100 | — | 100 | 5 | <3 | <3 | +++4,++1 | −5 |
| Glycerin | 100 | — | 100 | 10 | <3 | <3 | +++4,+1 | −5 |
| Propylene glycol | 100 | — | 100 | 10 | <3 | <3 | +++3,++1,+1 | +1,−4 |
| Ethanol | 5 | — | 100 | <5 | <3 | <3 | +++3,++2 | −5 |

Note:
*The TNF activity according to the in vitro method could not be assayed due to the cytotoxic activity of the additive against the L—M cells.

COMPARATIVE EXAMPLE 2

As the sugar and sugar-related compounds to be used in the present invention, D-glucose, sodium D-glucuronate, trehalose and a hydroxyethyl starch (average molecular weight: about 200,000) were employed. As comparative additives, various sugars and sugar-related compounds which are well-known stabilizing agents for the solution of customary physiologically active substances were employed.

To aliquots of the same TNF solution as employed in Example 1, the above-mentioned sugar and sugar-related compounds were added, respectively. In this instance, with respect to each kind of solution, there were prepared two solutions having different concentrations, i.e., 10 mg/ml and 200 mg/ml. Each of the resulting TNF solutions was stored at 4° C. for 7 days, and subjected to assay of the TNF activity according to the in vitro method as mentioned before. The remaining TNF activity (%) was calculated in the same manner as in Example 1, based on the obtained value of the TNF activity.

The results are shown in Table 5.

TABLE 5

| Additive | Concentration (mg/ml) | Remaining activity (%) | Additive | Concentration (mg/ml) | Remaining activity (%) |
|---|---|---|---|---|---|
| Control (without stabilizing agent) | — | <3 | Inositol | 200 | <3 |
| D-Glucose | 200 | 89 | Gluconic acid (Na) | 200 | 20 |
| D-Glucuronic acid (Na) | 200 | 75 | D-Glucosamine (HCl) | 10 | 3 |
| Trehalose | 200 | 94 | Lactose | 200 | <3 |
| Hydroxyethyl starch | 200 | 63 | Maltose | 200 | <3 |
| D-Arabinose | 200 | <3 | Sucrose | 200 | <3 |
| D-Ribose | 200 | <3 | β-Cyclodextrin | 10 | <3 |
| D-Fructose | 200 | <3 | Chondroitin sulfuric acid A (Na) | 10 | 3 |
| D-Mannose | 200 | <3 | Dextran sulfuric acid (Na: MW about 60,000) | 10 | <3 |
| Sorbitol | 200 | <3 | | | |

As is apparent from Examples and Comparative Examples as described above, according to the method for stabilizing TNF of the present invention, the TNF activity can be stably maintained during the storage of TNF in the form of a solution and during the operations such as freezing, thawing, lyophilization, heat-treatment or the like.

What is claimed is:

1. A method for stabilizing Tumor Necrosis Factor, which comprises adding to an aqueous solution or powder containing Tumor Necrosis Factor an effective amount of a stabilizing agent selected from a nonionic surfactant, at least one substance selected from the group consisting of D-glucose, D-galactose, D-xylose, D-glucuronic acid, a salt of D-glucuronic acid, trehalose, a dextran and a hydroxyethyl starch, and mixtures thereof.

2. A method according to claim 1, wherein said stabilizing agent is a nonionic surfactant.

3. A method according to claim 2, which further comprises subjecting to lyophilization the aqueous solution having said nonionic surfactant added thereto.

4. A method according to claim 2, wherein said nonionic surfactant is added in an amount of about 1 μg to 1 mg per ml of the aqueous solution containing Tumor Necrosis Factor, said aqueous solution having a TNF activity of $10^2$ to $10^9$ units/ml.

5. A method according to claim 4, which further comprises subjecting to lyophilization the aqueous solution having said nonionic surfactant added thereto.

6. A method according to claim 4, wherein the amount of said nonionic surfactant is about 5 μg to 100 μg per ml.

7. A method according to claim 6, which further comprises subjecting to lyophilization the aqueous solution having said nonionic surfactant added thereto.

8. A method according to claim 2, wherein said nonionic surfactant has an HLB value of 9 to 20.

9. A method according to claim 8, wherein said nonionic surfactant is added in an amount of about 1 μg to 1 mg per ml of the aqueous solution containing Tumor Necrosis Factor, said aqueous solution having a TNF activity of $10^2$ to $10^9$ units/ml.

10. A method according to claim 9, which further comprises subjecting to lyophilization the aqueous solution having said nonionic surfactant added thereto.

11. A method according to claim 9, wherein the amount of said nonionic surfactant is about 5 μg to 100 μg per ml.

12. A method according to claim 11, which further comprises subjecting to lyophilization the aqueous solution having said nonionic surfactant added thereto.

13. A method according to claim 2, wherein said nonionic surfactant has an HLB value of 13 to 18.

14. A method according to claim 13, wherein said nonionic surfactant is added in an amount of about 1 μg to 1 mg per ml of the aqueous solution containing Tumor Necrosis Factor, said aqueous solution having a TNF activity of $10^2$ to $10^9$ units/ml.

15. A method according to claim 14, which further comprises subjecting to lyophilization the aqueous solution having said nonionic surfactant added thereto.

16. A method according to claim 14, wherein the amount of said nonionic surfactant is about 5 μg to 100 μg per ml.

17. A method according to claim 16, which further comprises subjecting to lyophilization the aqueous solution having said nonionic surfactant added thereto.

18. A method according to claim 2, wherein said nonionic surfactant is selected from a polyoxyethylene fatty acid ester, a polyoxyethylene alkyl ether, a polyoxyethylene alkylphenyl ether, a polyoxyethylene sorbitan fatty acid ester, a polyoxyethylene glycerin fatty acid ester, a polyoxyethylene hydrogenated castor oil, a polyoxyethylene castor oil, a polyoxyethylene polyoxypropylene alkyl ether, a polyoxyethylene polyoxypropylene block polymer, a sorbitan fatty acid ester, a sucrose fatty acid ester, a glycerin fatty acid ester and mixtures thereof.

19. A method according to claim 18, wherein said nonionic surfactant is added in an amount of about 1 μg to 1 mg per ml of the aqueous solution containing Tumor Necrosis Factor, said aqueous solution having a TNF activity of $10^2$ to $10^9$ units/ml.

20. A method according to claim 19, which further comprises subjecting to lyophilization the aqueous solution having said nonionic surfactant added thereto.

21. A method according to claim 19, wherein the amount of said nonionic surfactant is about 5 μg to 100 μg per ml.

22. A method according to claim 21, which further comprises subjecting to lyophilization the aqueous solution having said nonionic surfactant added thereto.

23. A method according to claim 2, wherein said nonionic surfactant is selected from a polyoxyethylene fatty acid ester having a saturated or unsaturated fatty acid residue with 8 to 20 carbon atoms in which the number of moles of added ethylene oxide is about 4 to 50, a polyoxyethylene alkyl ether having a saturated or unsaturated alkyl group with 8 to 20 carbon atoms in which the number of moles of added ethylene oxide is about 5 to 55, a polyoxyethylene alkylphenyl ether having a saturated or unsaturated alkyl group with 5 to 10 carbon atoms in which the number of moles of added ethylene oxide is about 5 to 55, a polyoxyethylene sorbitan fatty acid ester having a saturated or unsaturated fatty acid residue with 8 to 20 carbon atoms in which the number of moles of added ethylene oxide is about 5 to 50, a polyoxyethylene glycerin fatty acid ester having a saturated or unsaturated fatty acid residue with 8 to 20 carbon atoms in which the number of moles of added ethylene oxide is about 5 to 50, a polyoxyethylene hydrogenated castor oil or polyoxyethylene castor oil in which the number of moles of added ethylene oxide is about 20 to 150, a polyoxyethylene polyoxypropylene alkyl ether having a saturated or unsaturated alkyl group with 12 to 18 carbon atoms and having an ethylene oxide content of about 65 to 85% by weight, a polyoxyethylene polyoxypropylene block polymer having a number average molecular weight of about 3,000 to 15,000 and having an ethylene oxide content of about 65 to 85% by weight, a sorbitan fatty acid ester which is a mono- or sesqui-acid ester of sorbitan with a saturated or unsaturated fatty acid having 8 to 20 carbon atoms, a sucrose fatty acid ester or glycerin fatty acid ester which is mono-acid ester of sucrose or glycerin with a saturated or unsaturated fatty acid having 8 to 20 carbon atoms, and mixtures thereof.

24. A method according to claim 23, wherein said nonionic surfactant is added in an amount of about 1 μg to 1 mg per ml of the aqueous solution containing Tumor Necrosis Factor, said aqueous solution having a TNF activity of $10^2$ to $10^9$ units/ml.

25. A method according to claim 24, which further comprises subjecting to lyophilization the aqueous solution having said nonionic surfactant added thereto.

26. A method according to claim 24, wherein the amount of said nonionic surfactant is about 5 μg to 100 μg per ml.

27. A method according to claim 26, which further comprises subjecting to lyophilization the aqueous solution having said nonionic surfactant added thereto.

28. A method according to claim 23, wherein said nonionic surfactant is selected from a polyoxyethylene sorbitan fatty acid having a saturated or unsaturated fatty acid residue with 8 to 20 carbon atoms in which the number of moles of added ethylene oxide is about 5 to 50, a polyoxyethylene hydrogenated castor oil in which the number of moles of added ethylene oxide is about 20 to 150, a polyoxyethylene castor oil in which the number of moles of added ethylene oxide is about 20 to 150, a polyoxyethylene polyoxypropylene block a average molecular weight of about 3,000 to 15,000 and having an ethylene oxide content of about 65 to 85% by weight, and mixtures thereof.

29. A method according to claim 28, wherein said nonionic surfactant is added in an amount of about 1 μg to 1 mg per ml of the aqueous solution containing Tumor Necrosis Factor, said aqueous solution having a TNF activity of $10^2$ to $10^9$ units/ml.

30. A method according to claim 29, which further comprises subjecting to lyophilization the aqueous solution having said nonionic surfactant added thereto.

31. A method according to claim 29, wherein the amoung of said nonionic surfactant is about 5 μg to 100 μg per ml.

32. A method according to claim 31, which further comprises subjecting to lyophilization the aqueous solution having said nonionic surfactant added thereto.

33. A method according to claim 28, wherein said nonionic surfactant is selected from polyoxyethylene (20) sorbitan monooleate, polyoxyethylene (60) hydrogenated castor oil, polyoxyethylene polyoxypropylene block polymer having a number average melecular weight of about 8,350 and having an ethylene oxide content of 80% by weight, and mixtures thereof.

34. A method according to claim 33, wherein said nonionic surfactant is added in an amount of about 1 μg to 1 mg per ml of the aqueous solution containing Tumor Necrosis Factor, said aqueous solution having a TNF activity of $10^2$ to $10^9$ units/ml.

35. A method according to claim 34, which further comprises subjecting to lyophilization the aqueous solution having said nonionic surfactant added thereto.

36. A method according to claim 34, wherein the amount of said nonionic surfactant is about 5 μg to 100 μg per ml.

37. A method according to claim 36, which further comprises subjecting to lyophilization the aqueous solution having said nonionic surfactant added thereto.

38. A method according to claim 1, wherein said stabilizing agent is at least one substance selected from the group consisting of D-glucose, D-galactose, D-xylose, D-glucuronic acid, a salt of D-glucuronic acid, trehalose, a dextran and a hydroxyethyl starch.

39. A method according to claim 38, which further comprises subjecting to lyophilization the aqueous solution having said substance added thereto.

40. A method according to claim 38, wherein said substance is added in an amount of about 10 mg to 500 mg per ml of the aqueous solution containing Tumor Necrosis Factor, said aqueous solution having a TNF activity of $10^2$ to $10^9$ units/ml.

41. A method according to claim 40, which further comprises subjecting to lyophilization the aqueous solution having said substance added thereto.

42. A method according to claim 40, wherein the amount of said substance is about 100 mg to 500 mg per ml.

43. A method according to claim 42, which further comprises subjecting to lyophilization the aqueous solution having said substance added thereto.

44. A method according to claim 38, wherein said substance is trehalose.

45. A method according to claim 44, wherein said substance is added in an amount of about 10 mg to 500 mg per ml of the aqueous solution containing Tumor Necrosis Factor, said aqueous solution having a TNF activity of $10^2$ to $10^9$ units/ml.

46. A method according to claim 45, which further comprises subjecting to lyophilization the aqueous solution having said substance added thereto.

47. A method according to claim 45, wherein the amount of said substance is about 100 mg to 500 mg per ml.

48. A method according to claim 47, which further comprises subjecting to lyophilization the aqueous solution having said substance added thereto.

49. A stable aqueous solution or powder which contains Tumor Necrosis Factor and an effective amount of a stabilizing agent selected from a nonionic surfactant, at least one substance selected from the group consisting of D-glucose, D-galactose, D-xylose, D-glucuronic acid, a salt of D-glucuronic acid, trehalose, a dextran and a hydroxyethyl starch, and mixtures thereof.

50. A stable aqueous solution or powder according to claim 49, wherein said stabilizing agent is a nonionic surfactant.

51. A stable aqueous solution or powder according to claim 50, wherein said nonionic surfactant is contained in an amount of about 1 μg to 1 mg per ml of the aqueous solution itself containing Tumor Necrosis Factor, said aqueous solution having a TNF activity of $10^2$ to $10^9$ units/ml, or is contained in an amount of about 1 μg to 1 mg per ml of an aqueous solution having a TNF activity of $10^2$ to $10^9$ units/ml which solution is one obtained by dissolving the powder containing Tumor Necrosis Factor.

52. A stable aqueous solution or powder according to claim 51, wherein the amount of said nonionic surfactant is about 5 μg to 100 μg per ml of the aqueous solution itself containing Tumor Necrosis Factor or an aqueous solution obtained by dissolving the powder containing Tumor Necrosis Factor.

53. A stable aqueous solution or powder according to claim 50, wherein said nonionic surfactant has an HLB value of 9 to 20.

54. A stable aqueous solution or powder according to claim 53, wherein said nonionic surfactant is contained in an amount of about 1 μg to 1 mg per ml of the aqueous solution itself containing Tumor Necrosis Factor, said aqueous solution having a TNF activity of $10^2$ to $10^9$ units/ml, or is contained in an amount of about 1 μg to 1 mg per ml of an aqueous solution having a TNF activity of $10^2$ to $10^9$ units/ml which solution is one obtained by dissolving the powder containing Tumor Necrosis Factor.

55. A stable aqueous solution or powder according to claim 54, wherein the amount of said nonionic surfactant is about 5 μg to 100 μg per ml of the aqueous solution itself containing Tumor Necrosis Factor or an aqueous solution obtained by dissolving the powder containing Tumor Necrosis Factor.

56. A stable aqueous solution or powder according to claim 50, wherein said nonionic surfactant has an HLB value of 13 to 18.

57. A stable aqueous solution or powder according to claim 56, wherein said nonionic surfactant is contained in an amount of about 1 μg to 1 mg per ml of the aqueous solution itself containing Tumor Necrosis Factor, said aqueous solution having a TNF activity of $10^2$ to $10^9$ units/ml, or is contained in an amount of about 1 μg to 1 mg per ml of an aqueous solution having a TNF activity of $10^2$ to $10^9$ units/ml which solution is one obtained by dissolving the powder containing Tumor Necrosis Factor.

58. A stable aqueous solution or powder according to claim 57, wherein the amount of said nonionic surfactant is about 5 μg to 100 μg per ml of the aqueous solution itself containing Tumor Necrosis Factor or an aqueous solution obtained by dissolving the powder containing Tumor Necrosis Factor.

59. A stable aqueous solution or powder according to claim 50, wherein said nonionic surfactant is selected from a polyoxyethylene fatty acid ester, a polyoxyethylene alkyl ether, a polyoxyethylene alkylphenyl ether, a polyoxyethylene sorbitan fatty acid ester, a polyoxyethylene glycerin fatty acid ester, a polyoxyethylene hydrogenated castor oil, a polyoxyethylene castor oil, a polyoxyethylene polyoxypropylene alkyl ether, a polyoxyethylene polyoxypropylene block polymer, a sorbitan fatty acid ester, a sucrose fatty acid ester, a glycerin fatty acid ester, and mixtures thereof.

60. A stable aqueous solution or powder according to claim 59, wherein said nonionic surfactant is contained in an amount of about 1 μg to 1 mg per ml of the aqueous solution itself containing Tumor Necrosis Factor, said aqueous solution having a TNF activity of $10^2$ to $10^9$ units/ml, or is contained in an amount of about 1 μg to 1 mg per ml of an aqueous solution having a TNF activity of $10^2$ to $10^9$ units/ml which solution is one obtained by dissolving the powder containing Tumor Necrosis Factor.

61. A stable aqueous solution or powder according to claim 60, wherein the amount of said nonionic surfactant is about 5 μg to 100 μg per ml of the aqueous solution itself containing Tumor Necrosis Factor or an aqueous solution obtained by dissolving the powder containing Tumor Necrosis Factor.

62. A stable aqueous solution or powder according to claim 50, wherein said nonionic surfactant is selected from a polyoxyethylene fatty acid ester having a saturated or unsaturated fatty acid residue with 8 to 20 carbon atoms in which the number of moles of added ethylene oxide is about 4 to 50, a polyoxyethylene alkyl ether having a saturated alkyl group with 8 to 20 carbon atoms in which the number of moles of added ethylene oxide is about 5 to 55, a polyoxyethylene alkylphenyl ether having a saturated or unsaturated alkyl group with 5 to 10 carbon atoms in which the number of moles of added ethylene oxide is about 5 to 55, a polyoxyethylene sorbitan fatty acid ester having a saturated or unsaturated fatty acid residue with 8 to 20 carbon atoms in which the number of moles of added ethylene oxide is about 5 to 50, a polyoxyethylene glycerin fatty acid ester having a saturated or unsaturated fatty acid residue with 8 to 20 carbon atoms in which the number of moles of added ethylene oxide is about 5 to 50, a polyoxyethylene hydrogenated castor oil or polyoxyethylene castor oil in which the number of moles of added ethylene oxide is about 20 to 150, a polyoxyethylene polyoxypropylene alkyl ether having a saturated or unsaturated alkyl group with 12 to 18 carbon atoms and having an ethylene oxide content of about 65 to 85% by weight, a polyoxyethylene polyoxypropylene block polymer having a number average molecular weight of about 3,000 to 15,000 and having an ethylene oxide content of about 65 to 85% by weight, a sorbitan fatty acid ester which is a mono- or sesquiacid ester of sorbitan with a saturated or unsaturated fatty acid having 8 to 20 carbon atoms, a sucrose fatty acid ester or glycerin fatty acid ester which is a mono-acid ester of sucrose or glycerin with a saturated or unsaturated fatty acid having 8 to 20 carbon atoms, and mixtures thereof.

63. A stable aqueous solution or powder according to claim 62, wherein said nonionic surfactant is contained in an amount of about 1 μg to 1 mg per ml of the aqueous solution itself containing Tumor Necrosis Factor, said aqueous solution having a TNF activity of $10^2$ to $10^9$ units/ml, or is contained in an amount of about 1 μg to 1 mg per ml of an aqueous solution having a TNF activity of $10^2$ to $10^9$ units/ml which solution is one obtained by dissolving the powder containing Tumor Necrosis Factor.

64. A stable aqueous solution or powder according to claim 63, wherein the amount of said nonionic surfactant is about 5 μg to 100 μg per ml of the aqueous solution itself containing Tumor Necrosis Factor or an aqueous solution obtained by dissolving the powder containing Tumor Necrosis Factor.

65. A stable aqueous solution or powder according to claim 62, wherein said nonionic surfactant is selected from a polyoxyethylene sorbitan fatty acid ester having a saturated or unsaturated fatty acid residue with 8 to 20 carbon atoms in which the number of moles of added ethylene oxide is about 5 to 50, a polyoxyethylene hydrogenated castor oil in which the number of moles of added ethylene oxide is about 20 to 150, a polyoxyethylene castor oil in which the number of moles of added ethylene oxide is about 20 to 150, a polyoxyethylene polyoxypropylene block polymer having a number average molecular weight of about 3,000 to 15,000 and having an ethylene oxide content of about 65 to 85% by weight, and mixtures thereof.

66. A stable aqueous solution or powder according to claim 65, wherein said nonionic surfactant is contained in an amount of about 1 μg to 1 mg per ml of the aqueous solution itself containing Tumor Necrosis Factor, said aqueous solution having a TNF activity of $10^2$ to $10^9$ units/ml, or is contained in an amount of about 1 μg to 1 mg per ml of an aqueous solution having a TNF activity of $10^2$ to $10^9$ units/ml which solution is one obtained by dissolving the powder containing Tumor Necrosis Factor.

67. A stable aqueous solution or powder according to claim 66, wherein the amount of said nonionic surfactant is about 5 μg to 100 μg per ml of the aqueous solution itself containing Tumor Necrosis Factor or an aqueous solution obtained by dissolving the powder containing Tumor Necrosis Factor.

68. A stable aqueous solution or powder according to claim 65, wherein said nonionic surfactant is selected from polyoxyethylene (20) sorbitan monooleate, polyoxyethylene (60) hydrogenated castor oil, polyoxyethylene polyoxypropylene block polymer having a number average molecular weight of about 8,350 and having an ethylene oxide content of 80% by weight, and mixtures thereof.

69. A stable aqueous solution or powder according to claim 68, wherein said nonionic surfactant is contained in an amount of about 1 μg to 1 mg per ml of the aqueous solution itself containing Tumor Necrosis Factor, said aqueous solution having a TNF activity of $10^2$ to $10^9$ units/ml, or is contained in an amount of about 1 μg to 1 mg per ml of an aqueous solution having a TNF activity of $10^2$ to $10^9$ units/ml which solution is one obtained by dissolving the powder containing Tumor Necrosis Factor.

70. A stable aqueous solution or powder according to claim 69, wherein the amount of said nonionic surfactant is about 5 μg to 100 μg per ml of the aqueous solution itself containing Tumor Necrosis Factor or an aqueous solution obtained by dissolving the powder containing Tumor Necrosis Factor.

71. A stable aqueous solution or powder according to claim 49, wherein said stabilizing agent is at least one substance selected from the group consisting of D-glucose, D-galactose, D-xylose, D-glucuronic acid, a salt of D-glucuronic acid, trehalose, a dextran and a hydroxyethyl starch.

72. A stable aqueous solution or powder according to claim 71, wherein said substance is contained in an amount of about 10 mg to 500 mg per ml of the aqueous solution itself containing Tumor Necrosis Factor, said aqueous solution having a TNF activity of $10^2$ to $10^9$ units/ml, or is contained in an amount of about 10 mg to 500 mg per ml of an aqueous solution having a TNF activity of $10^2$ to $10^9$ units/ml which solution is one obtained by dissolving the powder containing Tumor Necrosis Factor.

73. A stable aqueous solution or powder according to claim 72, wherein the amount of said substance is about 100 mg to 500 mg per ml of the aqueous solution itself containing Tumor Necrosis Factor or an aqueous solution obtained by dissolving the powder containing Tumor Necrosis Factor.

74. A stable aqueous solution or powder according to claim 71, wherein said substance is trehalose.

75. A stable aqueous solution or powder according to claim 74, wherein said substance is contained in an amount of about 10 mg to 500 mg per ml of the aqueous solution itself containing Tumor Necrosis Factor, said aqueous solution having a TNF activity of $10^2$ to $10^9$ units/ml, or is contained in an amount of about 10 mg to 500 mg per ml of an aqueous solution having a TNF activity of $10^2$ to $10^9$ units/ml which solution is one obtained by dissolving the powder containing Tumor Necrosis Factor.

76. A stable aqueous solution or powder according to claim 75, wherein the amount of said substance is about 100 mg to 500 mg per ml of the aqueous solution itself containing Tumor Necrosis Factor or an aqueous solution obtained by dissolving the powder containing Tumor Necrosis Factor.

* * * * *